United States Patent
Saito et al.

(10) Patent No.: US 10,113,988 B2
(45) Date of Patent: Oct. 30, 2018

(54) GAS SENSOR (71) Applicant: NGK INSULATORS, LTD., Nagoya-shi, Aichi (JP)

(72) Inventors: Naoya Saito, Nagoya (JP); Takayuki Sekiya, Nissin (JP); Takeshi Omori, Aichi (JP); Sumiko Horisaka, Kyoto (JP)

(73) Assignee: NGK INSULATORS, LTD., Nagoya (JP)

( * ) Notice: Subject to any disclaimer, the term of this patent is extended or adjusted under 35 U.S.C. 154(b) by 15 days.

(21) Appl. No.: 14/636,254

(22) Filed: Mar. 3, 2015

(65) Prior Publication Data
US 2015/0253281 A1 Sep. 10, 2015

(30) Foreign Application Priority Data

Mar. 5, 2014 (JP) ................. 2014-042517

(51) Int. Cl.
*G01N 27/409* (2006.01)
*G01N 27/407* (2006.01)
*C04B 37/00* (2006.01)

(52) U.S. Cl.
CPC ......... *G01N 27/409* (2013.01); *C04B 37/005* (2013.01); *G01N 27/4071* (2013.01);
(Continued)

(58) Field of Classification Search
CPC ............ G01N 27/409; G01N 27/4071; G01N 33/0004–33/0075; C04B 37/005;
(Continued)

(56) References Cited

U.S. PATENT DOCUMENTS 5,763,763 A 6/1998 Kato et al.
6,537,431 B1 * 3/2003 Tatsumoto ............. B28B 1/002
204/421
(Continued)

FOREIGN PATENT DOCUMENTS

EP 0769693 A1 4/1997
EP 2333535 A1 6/2011
(Continued)

OTHER PUBLICATIONS

Keiichi Saji, Characteristics of Limiting Current-Type Oxygen Sensor, J. Electrochem. Soc. 134(10) (1987) 2430-2435, See Fig. 1.*
(Continued)

*Primary Examiner* — Gurpreet Kaur
*Assistant Examiner* — Joshua L Allen
(74) *Attorney, Agent, or Firm* — Global IP Counselors, LLP (57) ABSTRACT

Provided is a gas sensor free from an unbonded space being in communication with an internal space. A gas sensor, which includes a sensor element including a plurality of layers that are bonded and formed of an oxygen-ion conductive solid electrolyte and which reduces a predetermined gas component of a measurement gas to identify a concentration of the gas component on the basis of a current flowing through the solid electrolyte, includes an internal space in which a measurement gas having the ability to reduce the gas component is provided. Of the plurality of layers, an interlaminar bonding layer, which bonds a layer forming a bottom surface of the internal space and a layer forming a side surface of the internal space, projects into the internal space.

11 Claims, 7 Drawing Sheets

(52) U.S. Cl.
CPC .. *C04B 2237/068* (2013.01); *C04B 2237/348* (2013.01); *C04B 2237/592* (2013.01); *C04B 2237/62* (2013.01); *C04B 2237/88* (2013.01)

(58) Field of Classification Search
CPC ........ C04B 2237/592; C04B 2237/348; C04B 2237/068; C04B 2237/62; C04B 2237/88
See application file for complete search history.

(56) References Cited

U.S. PATENT DOCUMENTS

| | | |
|---|---|---|
| 8,646,306 B2 | 2/2014 | Shindo et al. |
| 2007/0214865 A1* | 9/2007 | Nakae ................... C04B 37/005 73/19.01 |
| 2007/0246359 A1* | 10/2007 | Sugiyama .......... G01N 27/4075 204/429 |
| 2008/0190767 A1* | 8/2008 | Nakae ................ G01N 27/4071 204/424 |
| 2009/0130437 A1* | 5/2009 | Murai .................... B32B 18/00 428/332 |
| 2009/0229978 A1* | 9/2009 | Mizutani .............. G01N 27/407 204/424 |
| 2009/0288852 A1 | 11/2009 | Hirokawa et al. |
| 2011/0147214 A1* | 6/2011 | Fujita ................. G01N 27/4071 204/424 |
| 2013/0255352 A1* | 10/2013 | Ohtsubo ................ G01R 31/28 73/1.06 |
| 2013/0260983 A1 | 10/2013 | Omori et al. |
| 2015/0219591 A1* | 8/2015 | Shimizu ............. G01N 27/4071 204/426 |
| 2015/0268188 A1* | 9/2015 | Murakami ......... G01N 27/4071 204/431 |

FOREIGN PATENT DOCUMENTS

| | | | |
|---|---|---|---|
| EP | 2363707 A1 | | 9/2011 |
| JP | 9-113484 A | | 5/1997 |
| JP | 2001-30219 A | | 2/2001 |
| JP | 2011-145285 A | | 7/2011 |
| JP | 2012-247390 A | | 12/2012 |
| JP | 2012247390 A | * | 12/2012 |
| JP | 2013-227192 A | | 11/2013 |

OTHER PUBLICATIONS

The Extended European Search Report for the corresponding European patent application No. 15157404.3 dated Jul. 8, 2015.

* cited by examiner

GAS SENSOR

BACKGROUND OF THE INVENTION

Field of the Invention

The present invention relates to a gas sensor, and more particularly, to a gas sensor including a three-chambered sensor element.

Background Information

Various gas sensors have been conventionally used to obtain the concentration of a desired gas component of a measurement gas. For example, a NOx sensor including a sensor element formed of an oxygen-ion conductive solid electrolyte such as zirconia ($ZrO_2$) is well known as a device that measures the NOx concentration of a measurement gas such as a combustion gas (for example, see Japanese Patent Application Laid-Open Nos. 2011-145285 and 09-113484 (1997)).

Japanese Patent Application Laid-Open No. 2011-145285 discloses a process of manufacturing a sensor element that forms a gas sensor for obtaining a NOx concentration through introduction of a measurement gas into a space (internal space) provided in the element. Also, Japanese Patent Application Laid-Open No. 09-113484 discloses a so-called three-chambered sensor element having three internal spaces.

As disclosed in Japanese Patent Application Laid-Open No. 2011-145285, a sensor element containing an oxygen-ion conductive solid electrolyte as its structural material is obtained through the following process. A plurality of ceramic green sheets, each containing an oxygen-ion conductive solid electrolyte as a ceramic main component, are prepared. Then, portions that eventually serve as, for example, internal spaces or other interior spaces are appropriately punched, and a paste is printed or applied onto each of the ceramic green sheets. Subsequently, the ceramic green sheets are bonded and laminated to form a laminated body. The laminated body is cut into elements to obtain element bodies, and then, the element bodies are fired.

Any unbonded portion present in the bonding and laminating of ceramic green sheets can unnecessarily form an undesirable minute space (also referred to as an unbonded space or microcavity) in a portion, which should be closed in the obtained sensor element. For example, if such an unbonded space is formed to be in communication with the internal space, a gas such as air (oxygen) that has entered the unbonded space may diffuse into the internal space while the gas sensor is operating, which possibly has an adverse effect on the measurement accuracy of the gas sensor.

The sensor element is naturally designed so as not to generate such an unbonded space. However, variations in application of a bonding paste during the manufacture or variations in lamination occurring after the application, in practice, may form an unbonded space in a sensor element.

It is confirmed that such an unbonded space tends to be formed in a three-chambered sensor element, as disclosed in Japanese Patent Application Laid-Open No. 09-113484 (1997), in such a manner of being in communication with a third internal space in which a measuring electrode is provided. Therefore, a defect associated with the presence of an unbonded space is likely to occur in such a three-chambered sensor element.

A specific example of such a defect is as follows. Oxygen present in a third internal space while a gas sensor is being used needs to be, in practice, only the resultant of the decomposition of NOx. Thus, in the activation of the gas sensor, oxygen needs to be discharged from the third internal space as quickly as possible to make the gas sensor available. Any oxygen diffusing into the third internal space from the unbonded space, however, results in a longer time (light-off time) from the activation of the gas sensor to the completion of the discharge. Another example is a NOx concentration value obtained as a value different from an actual value due to a sudden or intermittent influx of oxygen from an unbonded space into the third internal space while a gas sensor is being used.

SUMMARY

The present invention relates to a gas sensor, and more particularly, to the structure of a gas sensor including a three-chambered sensor element.

A gas sensor according to the present invention includes a sensor element including a plurality of layers that are bonded and formed of an oxygen-ion conductive solid electrolyte, and reduces a predetermined gas component of a measurement gas to identify a concentration of the gas component on the basis of a current flowing through the solid electrolyte. The sensor element includes at least one internal space, a measuring electrode that is provided in one of the at least one internal space and has the ability to reduce the gas component of the measurement gas, a first layer that is one of the plurality of layers and forms a bottom surface of the internal space, a second layer that is another of the plurality of layers and forms a side surface of the internal space, and an interlaminar bonding layer bonding the first layer and the second layer, the interlaminar bonding layer projecting into the internal space.

According to the present invention, in a sensor element included in a gas sensor, an interlaminar bonding layer that bonds a layer forming a bottom surface of an internal space, in which a measuring electrode is provided, and a layer forming a side surface of the internal space is provided to project into the internal space, thereby preventing the occurrence of a microcavity being in communication with the internal space. This achieves a gas sensor in which an increase in light-off time or abnormal measurements during the use of the sensor, for example, resulting from an influx of oxygen into the microcavity, are preferably prevented or reduced.

The present invention therefore has an object to provide a gas sensor free from an unbonded space being in communication with an internal space.

DESCRIPTION OF THE PREFERRED EMBODIMENTS

<Outline Configuration of Gas Sensor>

Figure 1:
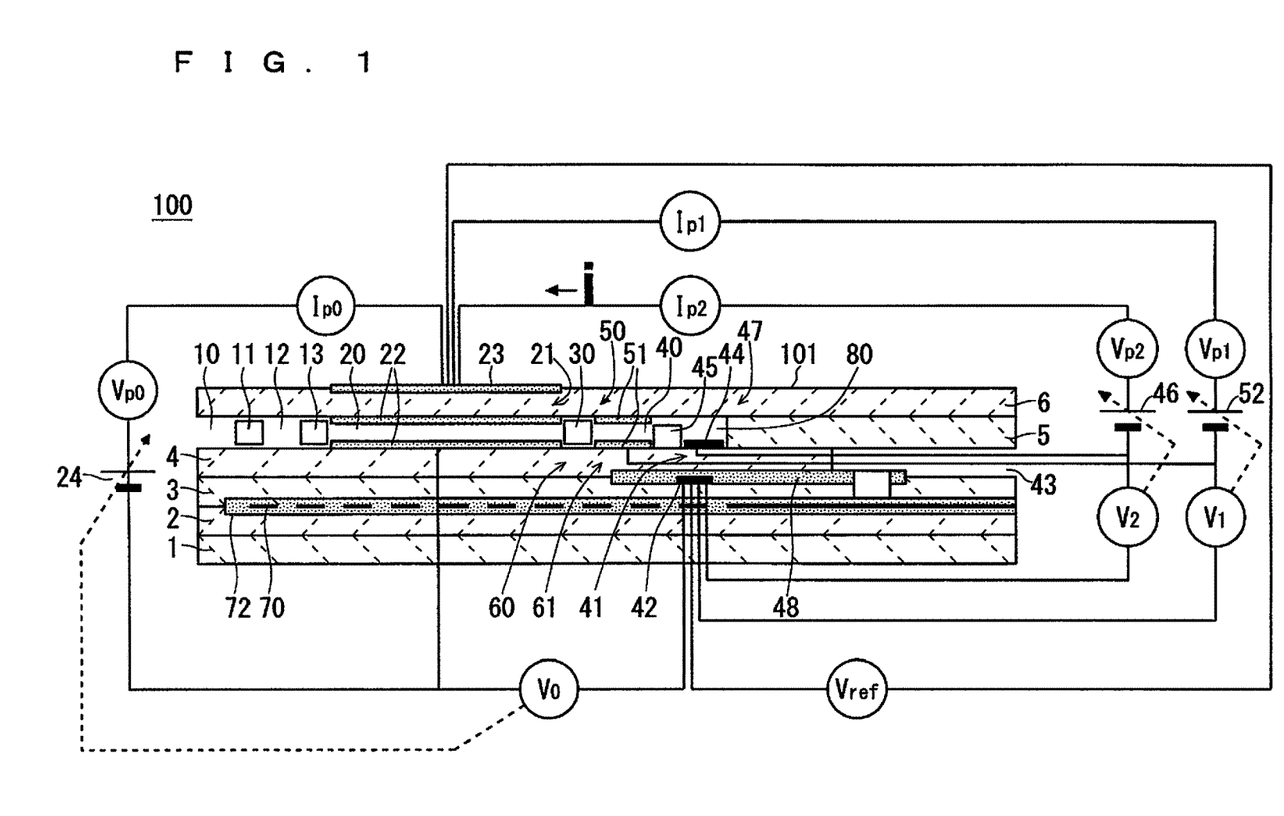
FIG. 1 is a cross-sectional view schematically showing the structure of a gas sensor 100, which is taken along the longitudinal direction of the gas sensor 100.

FIG. 1 is a cross-sectional view schematically showing the structure of a gas sensor 100 according to an embodiment of the present invention, which is taken along the longitudinal direction of the gas sensor 100. The gas sensor 100 according to this embodiment detects a predetermined to-be-measured gas component of a measurement gas and obtains the concentration of the gas component. A sensor element 101 being a main part thereof includes, as a structural material, ceramic mainly composed of zirconia being an oxygen-ion conductive solid electrolyte. The following description is given of an example in which a to-be-measured gas component is a NOx gas.

In outline, the sensor element 101 has the structure in which six layers, namely, a first substrate layer 1, a second substrate layer 2, a third substrate layer 3, a first solid electrolyte layer 4, a spacer layer 5, and a second solid electrolyte layer 6, each of the six layers formed of an oxygen-ion conductive solid electrolyte, are laminated in the stated order from the bottom side of the sheet of FIG. 1.

More specifically, the sensor element 101 is obtained by cutting a laminated body including ceramic green sheets corresponding to the six layers above, which are bonded and laminated with a zirconia-containing bonding paste, into elements and then firing the obtained individual element bodies. Though not shown FIG. 1, accordingly, a zirconia-containing interlaminar bonding layer (not shown) formed by firing the bonding paste is located between the six layers. In other words, the sensor element 101 can be regarded as having a configuration in which six layers, or, the first substrate layer 1, the second substrate layer 2, the third substrate layer 3, the first solid electrolyte layer 4, the spacer layer 5, and the second solid electrolyte layer 6, are bonded with interlaminar bonding layers to be laminated. It should be noted that organics present in the ceramic green sheet and the bonding paste evaporate and the sintering of ceramic advances during firing, and thus, the ceramic portions of the sensor element 101 including the interlaminar bonding layers are integrated irrespective of whether any of them derives from the ceramic green sheets or the bonding paste. Therefore, FIG. 1 shows boundaries between layers only for convenience' sake.

This embodiment is characterized in the form of an adjacent portion to a third internal space 80 (described below) of the interlaminar bonding layer located between the first solid electrolyte layer 4 and the spacer layer 5. This is described below in detail.

Provided between a lower surface of the second solid electrolyte layer 6 and an upper surface of the first solid electrolyte layer 4 on one-end-portion side of the sensor element 101 are a gas inlet 10, a first diffusion control part 11, a first internal space 20, a second diffusion control part 30, a second internal space 40, a third diffusion control part 45, and the third internal space 80. A buffer space 12 and a fourth diffusion control part 13 may be further provided between the first diffusion control part 11 and the first internal space 20. The gas inlet 10, the first diffusion control part 11, the buffer space 12, the fourth diffusion control part 13, the first internal space 20, the second diffusion control part 30, the second internal space 40, the third diffusion control part 45, and the third internal space 80 are adjacently formed so as to be in communication with one another in the stated order. The part extending from the gas inlet 10 to the third internal space 80 is referred to as a gas distribution part as well.

The gas inlet 10, the buffer space 12, the first internal space 20, the second internal space 40, and the third internal space 80 are interior spaces provided by hollowing out the spacer layer 5. The buffer space 12, the first internal space 20, the second internal space 40, and the third internal space 80 are each provided, with its upper portion defined by the lower surface of the second solid electrolyte layer 6, its lower portion defined by the upper surface of the first solid electrolyte layer 4, and its side portion defined by a side surface of the spacer layer 5.

The first diffusion control part 11, the second diffusion control part 30, the fourth diffusion control part 13, and the third diffusion control part 45 are each provided as two horizontally long slits (which are openings longitudinally extending perpendicular to the sheet of FIG. 1).

At a position that is located between an upper surface of the third substrate layer 3 and a lower surface of the spacer layer 5 and is farther from the distal-end side than the gas distribution part, a reference gas introduction space 43 is provided. The reference gas introduction space 43 is an interior space with its upper portion defined by the lower surface of the spacer layer 5, its lower portion defined by the upper surface of the third substrate layer 3, and its side portion defined by a side surface of the first solid electrolyte layer 4. For example, oxygen or air is introduced into the reference gas introduction space 43 as a reference gas.

The gas inlet 10 is a part being open to the outside. Through this gas inlet 10, a measurement gas is taken into the sensor element 101 from the outside.

The first diffusion control part 11 is a part that applies a predetermined diffusion resistance to the measurement gas taken through the gas inlet 10. Alternatively, without the gas inlet 10, the sensor element 101 may be configured such that the end of the first diffusion control part 11 is positioned at the end of the sensor element 101, and the first diffusion control part 11 may serve as the gas inlet 10.

The buffer space 12 is provided to cancel concentration fluctuations of the measurement gas which are caused due to pressure fluctuations of the measurement gas in the outside (in the case where the measurement gas is a vehicle exhaust gas, pulsations of the exhaust gas pressure). The sensor element 101 does not necessarily need to include the buffer space 12.

The fourth diffusion control part 13 is a part that applies a predetermined diffusion resistance to the measurement gas introduced into the first internal space 20 from the buffer space 12. The fourth diffusion control part 13 is a part provided in association with the provision of the buffer space 12.

The first diffusion control part 11 and the first internal space 20 are directly in communication with each other if the buffer space 12 and the fourth diffusion control part 13 are not provided.

The first internal space 20 is provided as a space for adjusting an oxygen partial pressure of the measurement gas introduced through the gas inlet 10. This oxygen partial pressure is adjusted through the operation of a main pumping cell 21.

The main pumping cell 21 is an electrochemical pumping cell (first electrochemical pumping cell) formed of an inside pump electrode 22, an outside pump electrode 23, and the oxygen-ion conductive solid electrolyte sandwiched between these electrodes. The inside pump electrode 22 is provided on substantially the entire upper surface of the first solid electrolyte layer 4, substantially the entire lower surface of the second solid electrolyte layer 6, and substantially the entire side surface of the spacer layer 5, these surfaces defining the first internal space 20. The outside pump electrode 23 is provided so as to be exposed to the outside in the region corresponding to the inside pump electrode 22 on the upper surface of the second solid electrolyte layer 6. The inside pump electrode 22 and the outside pump electrode 23 are each formed as a porous cermet electrode rectangular in plan view (for example, a cermet electrode made of $ZrO_2$ and a precious metal such as Pt containing 0.1 wt % to 30.0 wt % Au). The inside pump electrode 22 is formed of a material having a lower ability to reduce a NO component of the measurement gas or having no reducing ability. In other words, the inside pump electrode 22 is formed as a low-NO-reducing pump electrode having a limited ability to reduce a NO component.

The main pumping cell 21 causes, upon application of a pump voltage Vp0 by a variable power source 24 provided outside the sensor element 101, a pump current Ip0 to flow between the outside pump electrode 23 and the inside pump electrode 22 in the positive direction or the negative direction, allowing oxygen in the first internal space 20 to be pumped out to the outside or outside oxygen to be pumped into the first internal space 20.

In the sensor element 101, the inside pump electrode 22, a reference electrode 42 sandwiched between the upper surface of the third substrate layer 3 and the first solid electrolyte layer 4, and the oxygen-ion conductive solid electrolyte sandwiched between these electrodes constitute a first oxygen-partial-pressure detection sensor cell 60 being an electrochemical sensor cell. The reference electrode 42 is an electrode substantially rectangular in plan view, which is formed of a porous cermet similar to, for example, the outside pump electrode. Provided around the reference electrode 42 is a reference gas introduction layer 48 that is made of porous alumina and is continuous with the reference gas introduction space 43, so that the reference gas of the reference gas introduction space 43 is introduced to the surface of the reference electrode 42. In the first oxygen-partial-pressure detection sensor cell 60, an electromotive force V0 is generated between the inside pump electrode 22 and the reference electrode 42, which results from an oxygen concentration difference between the atmosphere in the first internal space 20 and the reference gas of the reference gas introduction space 43.

The electromotive force V0 generated in the first oxygen-partial-pressure detection sensor cell 60 varies in accordance with the oxygen partial pressure in the atmosphere present in the first internal space 20. The sensor element 101 uses this electromotive force V0 to feedback-control the variable power source 24 for the main pumping cell 21. This allows the pump voltage Vp0, which is applied to the main pumping cell 21 by the variable power source 24, to be controlled in accordance with the oxygen partial pressure in the atmosphere of the first internal space 20. The sensor element 101 according to this embodiment controls the pump voltage Vp0 to be applied to the main pumping cell 21 by the variable power source 24 such that the oxygen partial pressure in the atmosphere of the first internal space 20 has a predetermined value sufficiently low enough to control an oxygen partial pressure in the second internal space 40.

The second diffusion control part 30 is a part that applies a predetermined diffusion resistance to the measurement gas introduced into the second internal space 40 from the first internal space 20.

The second internal space 40 is provided as a space for performing the process for causing an inflammable gas component of the measurement gas introduced through the second diffusion control part 30 to contain only a hydrocarbon gas.

An auxiliary pumping cell 50 is an auxiliary electrochemical pumping cell (second electrochemical pumping cell) formed of an auxiliary pump electrode 51, the outside pump electrode 23, and the oxygen-ion conductive solid electrolyte sandwiched between these electrodes. The auxiliary pump electrode 51 is provided on substantially the entire upper surface of the first solid electrolyte layer 4, the lower surface of the second solid electrolyte layer 6, and substantially the entire side surface of the spacer layer 5, the surfaces defining the second internal space 40. The auxiliary pump electrode 51 is formed as a porous cermet electrode rectangular in plan view, similarly to the outside pump electrode 23 and the inside pump electrode 22. The use of the outside pump electrode 23 is not necessarily required, and another cermet electrode provided on the outer surface of the sensor element 101 may form an outside pump electrode of the auxiliary pumping cell 50, in place of the outside pump electrode 23.

The auxiliary pumping cell 50 causes, upon application of a pump voltage Vp1 by a variable power source 52 provided outside the sensor element 101, a pump current Ip1 to flow between the outside pump electrode 23 and the auxiliary pump electrode 51 in the positive direction, so that oxygen can be pumped out of the second internal space 40.

In the sensor element 101, the auxiliary pump electrode 51, the reference electrode 42, and the oxygen-ion conductive solid electrolyte sandwiched between these electrodes constitute a second oxygen-partial-pressure detection sensor cell 61 being an electrochemical sensor cell. In the second oxygen-partial-pressure detection sensor cell 61, an electromotive force V1 is generated between the auxiliary pump electrode 51 and the reference electrode 42, which results from an oxygen concentration difference between the atmosphere in the second internal space 40 and the reference gas (air) of the reference gas introduction space 43.

The electromotive force V1 to be generated in the second oxygen-partial-pressure detection sensor cell 61 varies in accordance with the oxygen partial pressure in the atmosphere present in the second internal space 40. The sensor element 101 uses this electromotive force V1 to feedback-control the variable power source 52 for the auxiliary pumping cell 50. This allows the pump voltage Vp1, which is applied to the auxiliary pumping cell 50 by the variable power source 52, to be controlled in accordance with the oxygen partial pressure in the atmosphere present in the second internal space 40. The sensor element 101 according to this embodiment controls the pump voltage Vp1 applied to the auxiliary pumping cell 50 by the variable power source 52 such that the oxygen partial pressure in the atmosphere of the second internal space 40 has a predetermined value sufficiently low enough to have substantially no influence on the measurement of the NOx concentration.

The third diffusion control part 45 is a part that applies a predetermined diffusion resistance to the measurement gas introduced into the third internal space 80 from the second internal space 40.

The third internal space 80 is provided as a space for performing the process for measuring the concentration of a NOx gas in the measurement gas introduced through the third diffusion control part 45. The sensor element 101 can pump out oxygen present in the third internal space 80 through the operation of a measuring pumping cell 47. The measuring pumping cell 47 is an electrochemical pumping cell (measuring pumping cell) including the outside pump electrode 23, a measuring electrode 44, and the oxygen-ion conductive solid electrolyte sandwiched between these electrodes.

The measuring electrode 44 is a porous cermet electrode substantially rectangular in plan view, which is included in the third internal space 80. The measuring electrode 44 is formed of a metal capable of reducing a NOx gas and a porous cermet made of zirconia. Pt, which is a main component, containing Rh can be used as a metal component. This causes the measuring electrode 44 to also function as a NOx reducing catalyst that reduces NOx present in the atmosphere of the third internal space 80. The measuring electrode 44 generates oxygen through the reduction or decomposition of NOx of the measurement gas by catalytic activation.

The sensor element 101 includes a measuring sensor cell 41. The measuring sensor cell 41 is an electrochemical sensor cell composed of the measuring electrode 44, the reference electrode 42, and the oxygen-ion conductive solid electrolyte sandwiched between these electrodes. The measuring sensor cell 41 generates an electromotive force V2 between the measuring electrode 44 and the reference electrode 42 in accordance with the oxygen concentration difference between the atmosphere of the third internal space 80 (in particular, the atmosphere in the vicinity of the surface of the measuring electrode 44) and the reference gas of the reference gas introduction space 43. The sensor element 101 uses this electromotive force V2 to feedback-control the variable power source 46 for the measuring pumping cell 47 provided outside the sensor element 101. This allows the pump voltage Vp2, which is applied to the measuring pumping cell 47 by the variable power source 46, to be controlled in accordance with the oxygen partial pressure in the atmosphere of the third internal space 80.

The measurement gas reaches the third internal space 80 after oxygen is pumped out of the first internal space 20 and the second internal space 40. It means that oxygen, which is present in the atmosphere of the third internal space 80, is generated through the decomposition of NOx in the measuring electrode 44. Thus, the current (NOx current) Ip2 flowing through the measuring pumping cell 47 is substantially proportional to the NOx concentration of the measurement gas (the NOx current Ip2 and the NOx concentration are in a linear relationship). The sensor element 101 detects such a NOx current Ip2 and obtains the NOx concentration of the measurement gas on the basis of the pre-identified functional relationship (linear relationship) between the NOx current Ip2 and the NOx concentration.

The sensor element 101 is configured to measure an electromotive force $V_{ref}$ generated between the outside pump electrode 23 and the reference electrode 42 to obtain the oxygen partial pressure outside the sensor element 101.

In the sensor element 101, further, a heater 70 is formed to be vertically sandwiched between the second substrate layer 2 and the third substrate layer 3. The heater 70 generates heat by power feeding from the outside through a heater electrode (not shown) provided on the lower surface of the first substrate layer 1. Heat generation by the heater 70 increases the oxygen-ion conductivity of the solid electrolyte forming the sensor element 101. The heater 70 is buried over the entire area extending from the first internal space 20 to the second internal space 40 to heat a predetermined portion of the sensor element 101 to a predetermined temperature or maintain the temperature of the predetermined portion at a predetermined temperature. Formed on the upper and lower surfaces of the heater 70 is a heater insulating layer 72 made of, for example, alumina to obtain electrical insulation between the second substrate layer 2 and the third substrate layer 3 (hereinafter, the heater 70, the heater electrode, and the heater insulating layer 72 are correctively referred to as a heater part as well).

<Forms of Interlaminar Bonding Layer in and Near Third Internal Space>

Figure 2A:
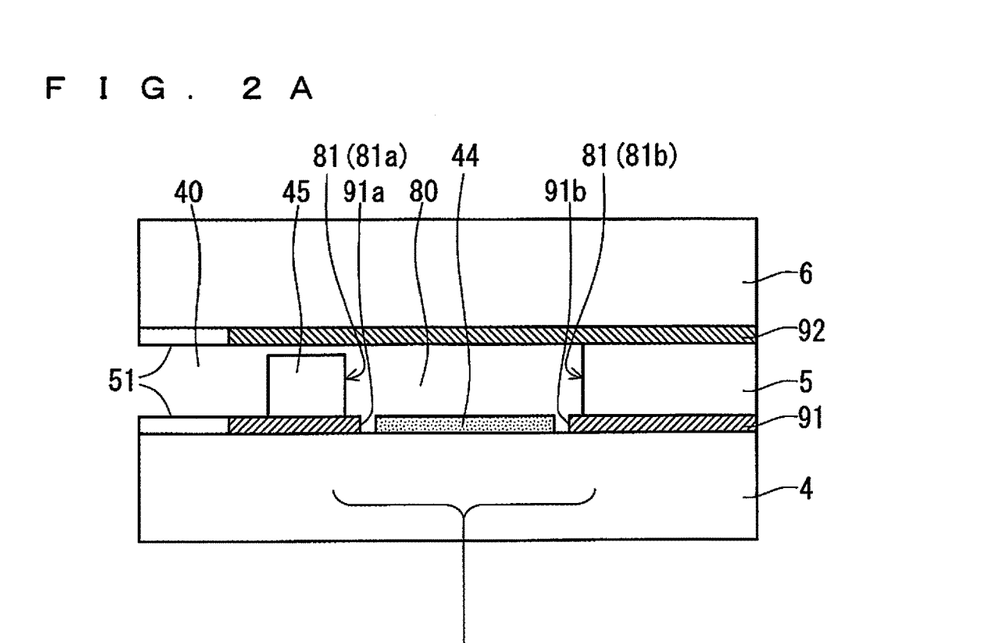
FIGS. 2A and 2B are partial detail views of a third internal space 80 and its adjacent portion of a sensor element 101 provided with an interlaminar bonding layer 91 in a first form.
Figure 2B:
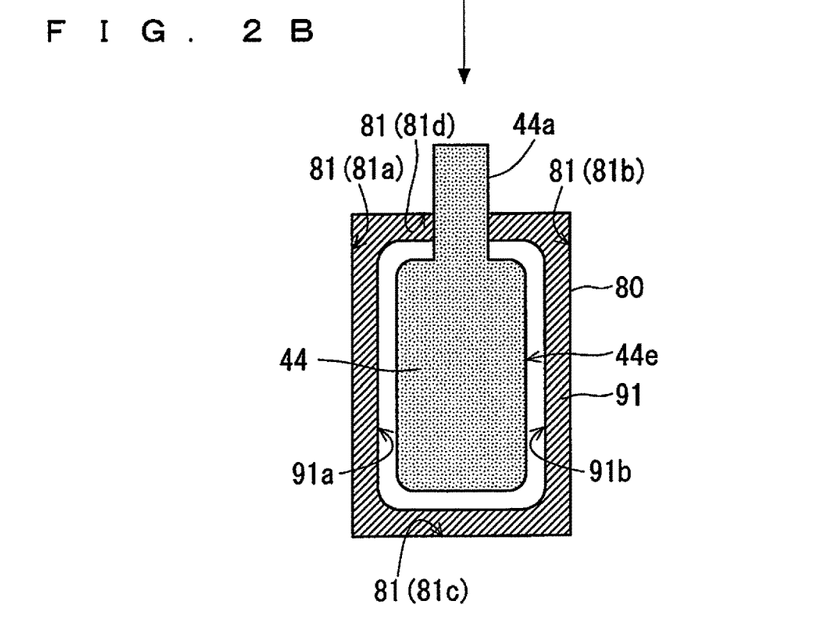
Figure 3A:
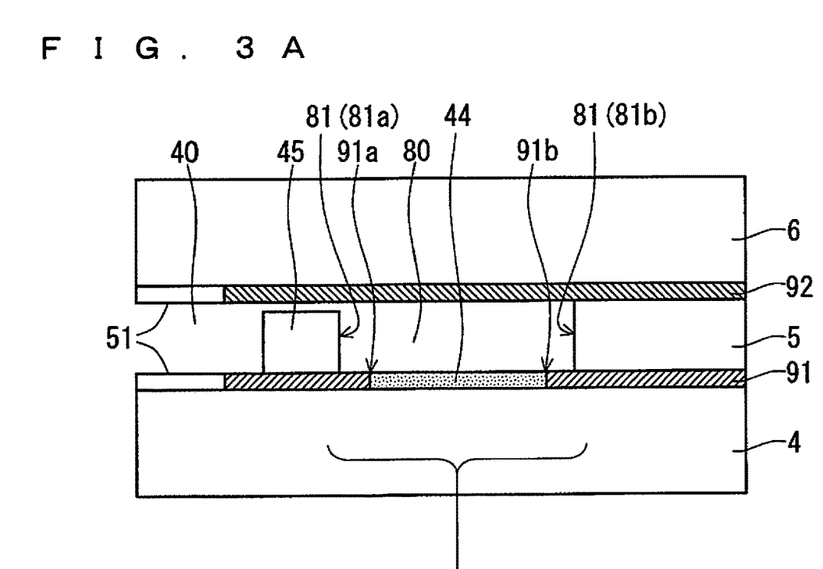
FIGS. 3A and 3B are partial detail views of the third internal space 80 and its adjacent portion of the sensor element 101 provided with the interlaminar bonding layer 91 in a second form.
Figure 3B:
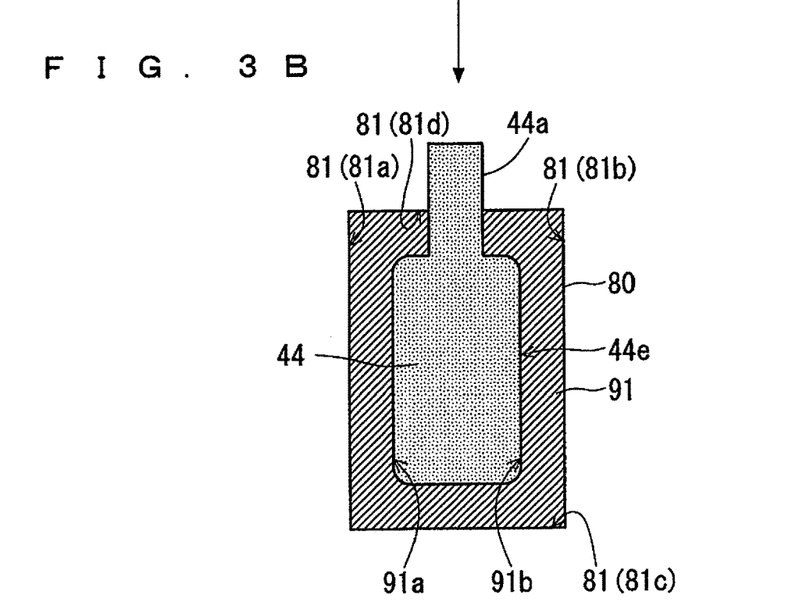
Figure 4A:
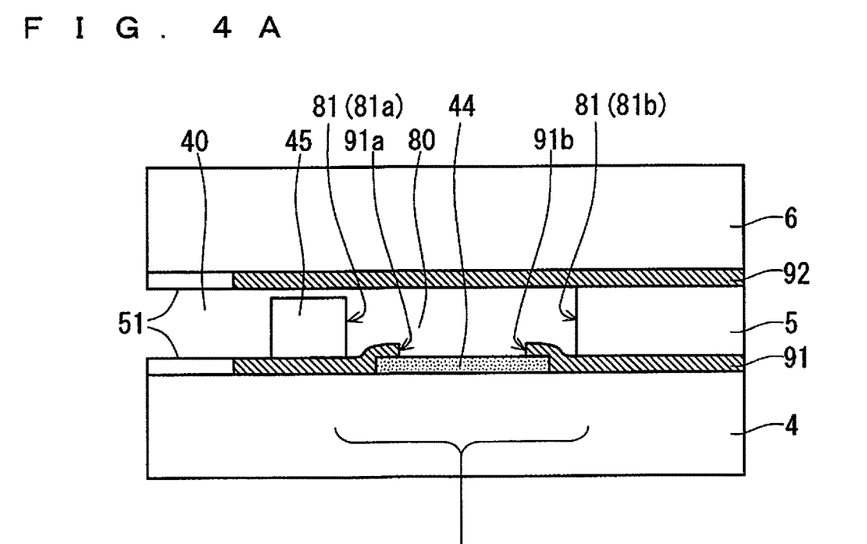
FIGS. 4A and 4B are partial detail views of the third internal space 80 and its adjacent portion of the sensor element 101 provided with the interlaminar bonding layer 91 in a third form.
Figure 4B:
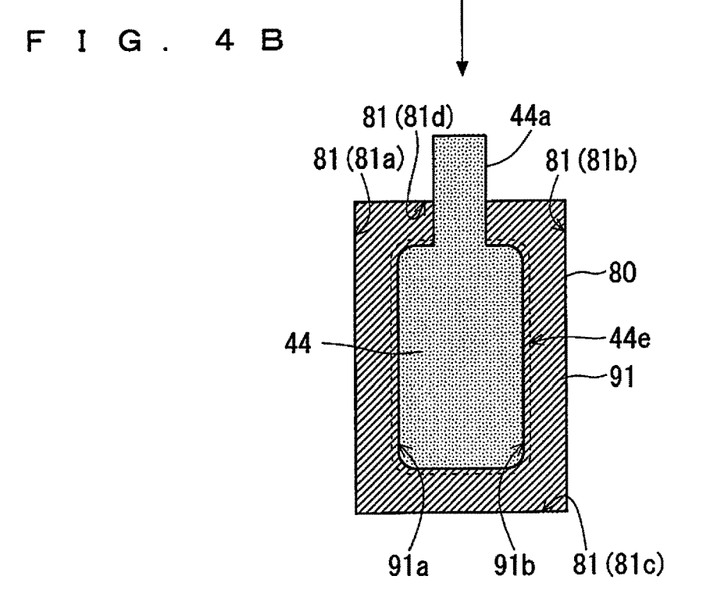

FIGS. 2A and 2B, 3A and 3B, and 4A and 4B are partial detail views of the third internal space 80 and its adjacent portion of the sensor element 101. FIGS. 2A, 3A, and 4A are longitudinal partial cross-sectional views, and FIGS. 2B, 3B, and 4B are partial plan views also showing the upper surface of the measuring electrode 44.

The third internal space 80 has a bottom surface formed of the first solid electrolyte layer 4 and an upper surface formed of the second solid electrolyte layer 6 and is a space rectangular in plan view, which is defined by four side surfaces 81 (81a, 81b, 81c, and 81d) provided in the spacer layer 5. The measuring electrode 44 is provided in the portion that is the center in a plan view of the third internal space 80 and is on the upper surface of the first solid electrolyte layer 4. From one end of the measuring electrode 44, a lead 44a for electrical connection with the outside extends to be connected with a terminal electrode (not shown) provided on the outer surface of the sensor element 101.

As shown in FIGS. 2A, 3A, and 4A, interlaminar bonding layers 91 and 92, each bonding its vertically adjoining layers, are located between the first solid electrolyte layer 4 and the spacer layer 5 and between the spacer layer 5 and the second solid electrolyte layer 6, respectively. Each of the interlaminar bonding layers 91 and 92 is a ceramic layer formed by firing a bonding paste applied for bonding ceramic green sheets that form the respective solid electrolyte layers. The interlaminar bonding layer is similarly located between the first substrate layer 1, the second substrate layer 2, the third substrate layer 3, and the first solid electrolyte layer 4.

In the sensor element 101 according to this embodiment, all the interlaminar bonding layers including the interlaminar bonding layer 92 except for the interlaminar bonding layer 91 are formed to entirely cover an area corresponding to the upper surface portion of the third internal space 80 as in the conventional sensor element.

The interlaminar bonding layer 91 formed between the first solid electrolyte layer 4 and the spacer layer 5 is characterized in that it is formed to project from the side surface 81 of the third internal space 80 into the third internal space 80, in addition to being formed to bond the first solid electrolyte layer 4 and the spacer layer 5. In other words, the interlaminar bonding layer 91 is formed to be exposed to the third internal space 80. This formation can be achieved by, in the manufacture of the sensor element 101, determining the application area of the bonding paste that is to serve as the interlaminar bonding layer 91 such that the area extends into the area that is to serve as the upper surface of the third internal space 80, prior to the application of the bonding paste to the ceramic green sheet that is to serve as the first solid electrolyte layer 4.

Specific forms of the interlaminar bonding layer 91 include three forms shown in FIGS. 2A to 4B.

(First Form)

First, in the first form shown in FIG. 2 FIGS. 2A and 2B, the interlaminar bonding layer 91 is formed to be apart from the measuring electrode 44 while it projects from the side surface 81 of the third internal space 80 into the third internal space 80. For example, with reference to FIG. 2A, edges 91a and 91b of the interlaminar bonding layer 91 are located closer to an outer peripheral edge 44e of the measuring electrode 44 than the side surfaces 81 a and 81b of the third internal space 80 that are opposed to each other in the longitudinal direction of the sensor element 101. Also, FIG. 2B reveals that the same holds true for the relationship between the interlaminar bonding layer 91 and the side surfaces 81c and 81d of the third internal space 80 that are opposed to each other in the transverse direction of the sensor element 101.

(Second Form)

Next, in the second form shown in FIG. 3 FIGS. 3A and 38, the interlaminar bonding layer 91 is formed to project from the side surface 81 of the third internal space 80 into the third internal space 80 and to come into contact with the measuring electrode 44 without a gap. For example, with reference to FIG. 3A, the edges 91a and 91b of the interlaminar bonding layer 91 are in contact with the outer peripheral edge 44e of the measuring electrode 44. Also, FIG. 3B reveals that the same holds true for the relationship between the interlaminar bonding layer 91 and the side surfaces 81c and 81d of the third internal space 80 that are opposed to each other in the transverse direction of the sensor element 101.

(Third Form)

In the third form shown in FIG. 4 FIGS. 4A and 4B, the interlaminar bonding layer 91 is formed to extend to the inside of the side surface 81 of the third internal space 80 in plan view and to overlap and cover the outer peripheral portion of the measuring electrode 44. For example, with reference to FIG. 4A, the edges 91a and 91b of the interlaminar bonding layer 91 cover the outer peripheral edge 44e of the measuring electrode 44. Also, FIG. 4B reveals that the same holds true for the relationship between the interlaminar bonding layer 91 and the side surfaces 81c and 81d of the third internal space 80 that are opposed to each other in the transverse direction of the sensor element 101.

An excessively large overlapping portion between the interlaminar bonding layer 91 and the measuring electrode 44 may damage the function of the measuring electrode 44. Therefore, the overlapping portion is preferably about 20% or less of the measuring electrode 44 at most.

(Conventional Form)

Figure 5A:
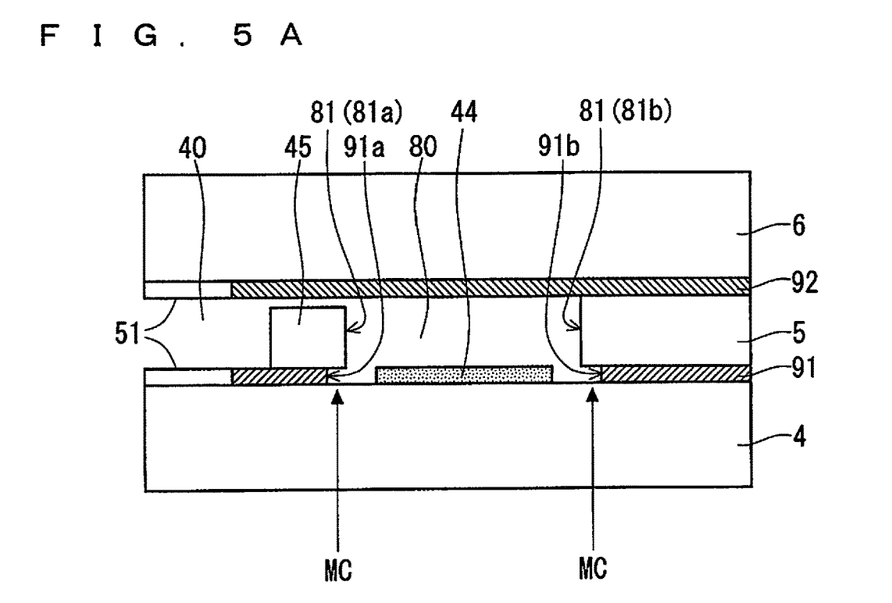
FIGS. 5A and 5B are partial detail views of the third internal space 80 and its adjacent portion of the sensor element 101 provided with the interlaminar bonding layer 91 in a conventional form.
Figure 5B:
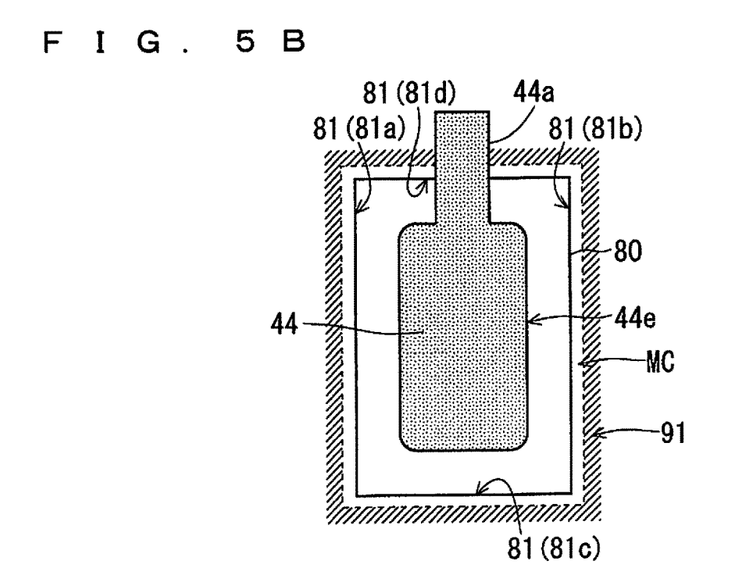

Shown in FIGS. 5A and 5B, which are partial detail views of the third internal space 80 and its adjacent portion of the sensor element 101 in the case where, as a conventional example of the formation of an interlaminar bonding layer 91, a bonding paste for interlaminar bonding layer 91 is applied on the assumption that an edge of the interlaminar bonding layer 91 and the side surface of the third internal space 80 are located at the same position in plan view.

When the interlaminar bonding layer 91 is provided in such a form, in the sensor element 101, the interlaminar bonding layer 91 may be formed at a position farther from the outer peripheral edge 44e than the side surface 81 of the third internal space 80. Consequently, a microcavity MC being an unjoined (unbonded) portion may be formed to be in communication with the third internal space 80 between the first solid electrolyte layer 4 and the spacer layer 5.

For example, in the case shown in FIG. 5A, the edges 91a and 91b of the interlaminar bonding layer 91 are farther from the outer peripheral edge 44e of the measuring electrode 44 than the side surfaces 81a and 81b of the third internal space 80, and a microcavity MC being an unjoined (unbonded) portion is formed to be in communication with the third internal space 80 between the first solid electrolyte layer 4 and the spacer layer 5. FIG. 5B illustrates a case in which the side surfaces 81c and 81d of the third internal space 80 that are opposed to each other in the transverse direction of the sensor element 101 and the interlaminar bonding layer 91 have a positional relationship as described above, and a microcavity MC is formed to surround the third internal space 80.

For brevity of description, FIG. 5B shows the microcavity MC linearly formed with a uniform width at all of the four side surfaces 81a, 81b, 81c, and 81d of the third internal space 80. In practice, however, a microcavity MC may be formed in an irregular shape at an appropriate position around the third internal space 80.

The presence of such a microcavity MC is not preferable because it allows an influx of oxygen (air) while the gas sensor 100 is not being used, and oxygen slowly leaks from the microcavity MC while oxygen is being discharged from the third internal space 80 in activation of the gas sensor 100, resulting in a longer light-off time being a time from the activation of the gas sensor 100 to the completion of the discharge. Additionally, the presence of a microcavity MC is not preferable because oxygen (air) left in the microcavity MC suddenly or intermittently flows into the third internal space 80 from the microcavity MC during the operation of the gas sensor 100, resulting in a NOx concentration value different from an actual value.

In this embodiment, in view of the problems above, the interlaminar bonding layer 91 is provided to project from the side surface 81 of the third internal space 80 into the third internal space 80 as in the first to the third forms. This preferably prevents or reduces an increase in light-off time or abnormal measurements during the use of a sensor, for example, resulting from an influx of oxygen into a microcavity MC, in the gas sensor 100 according to this embodiment, because the microcavity MC being in communication with the third internal space 80 is not formed.

A microcavity is likely to be formed around the first internal space 20 and the second internal space 40, and thus, the interlaminar bonding layer 91 may be formed in these internal spaces as in the first to third forms. In the first internal space 20 and the second internal space 40, however, the main pumping cell 21 and the auxiliary pumping cell 50 remove oxygen in a measurement gas as much as possible. Thus, if oxygen is included in a formed microcavity, the oxygen is sufficiently removed through the operations of the main pumping cell 21 and the auxiliary pumping cell 50. Therefore, the above-mentioned form is not necessarily required.

In the sensor element including only two internal spaces, namely, the first internal space 20 and the second internal space 40, and including the measuring electrode 44 provided in the second internal space 40, the interlaminar bonding layer 91 in the two internal spaces may be formed as in the first to third forms.

As described above, according to this embodiment, in the case where a gas sensor includes a three-chambered sensor element, an interlaminar bonding layer that bonds a layer forming the bottom surface of a third internal space, in which a measuring electrode is provided, and a layer forming a side surface is provided to project into the third internal space, thereby preventing the occurrence of a microcavity being in communication with the third internal space. This achieves a gas sensor in which an increase in light-off time or abnormal measurements during the use of the sensor, for example, resulting from an influx of oxygen into the microcavity, are preferably prevented or reduced.

EXAMPLES

Example 1

Light-off time was measured for a sensor element 101 including an interlaminar bonding layer 91 provided in the first form and a conventional sensor element including an interlaminar bonding layer 91 provided in the conventional form. In this example, a time, at which a concentration value reached a value 10 ppm higher than a saturation value of residual oxygen concentration in a third internal space 80 after the activation of a gas sensor, is defined as a light-off time.

Figure 6A:
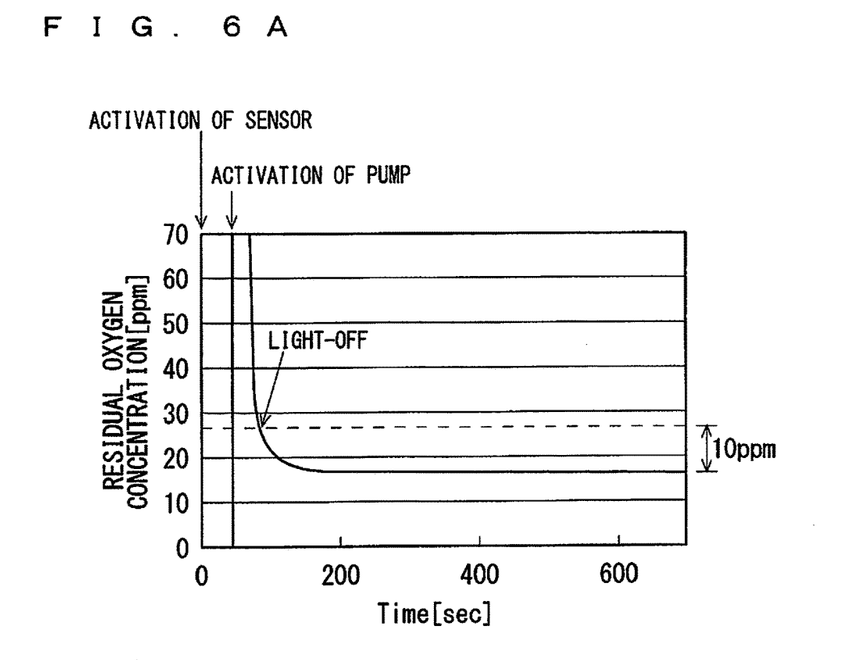
FIGS. 6A and 6B show the results of Example 1.
Figure 6B:
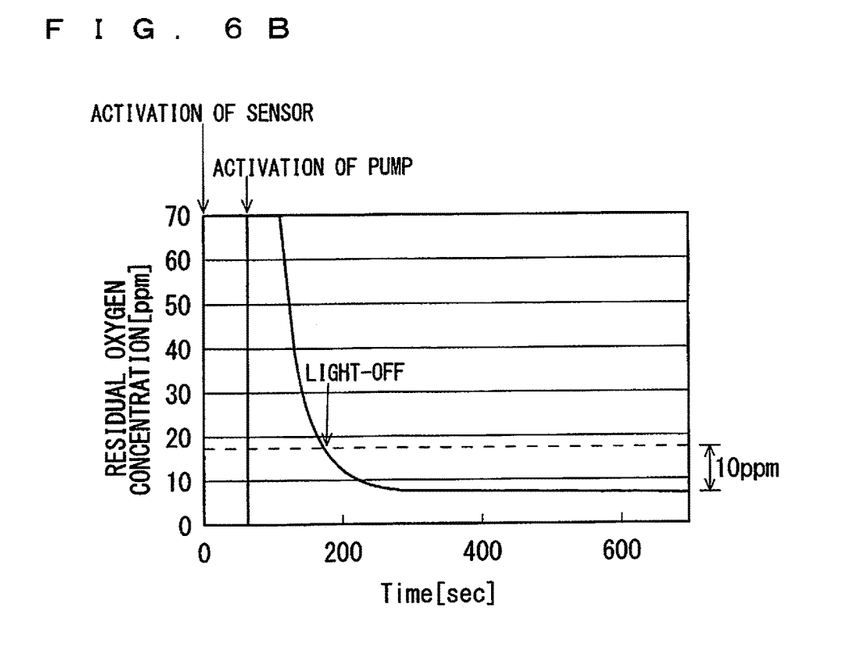

FIGS. 6A and 6B show how light-off time was measured for the respective sensor elements. The vertical lines of FIGS. 6A and 6B represent the residual oxygen concentration of the third internal space 80. In the gas sensor 100, the energization of the heater 70 is started in activation, whereas the energization of each pump cell is performed after a lapse of a predetermined time since the activation. This is because, due to the temperature dependence of a resistance value of the sensor element 101, each pump cell will not operate preferably unless the temperature of the sensor element 101 rises to some extent. FIGS. 6A and 6B show the timing at which the heater 70 is activated (the gas sensor 100 is activated) as "activation of sensor" and show the timing at which each pump cell is activated as "activation of pump."

FIG. 6A shows the results on the sensor element 101 in the first form. The light-off time of the sensor element 101 is approximately 80 seconds.

FIG. 6B, meanwhile, shows the results on the sensor element in the conventional form. The light-off time of the sensor element is approximately 180 seconds.

These results show that providing the interlaminar bonding layer 91 in the first form is effective at preventing an increase in light-off time.

Example 2

Six sensor elements 101 each including an interlaminar bonding layer 91 provided in the second form were prepared, and four sensor elements each including an interlaminar bonding layer 91 provided in the conventional form were prepared. Then, light-off time was measured for all of the sensor elements.

Figure 7:
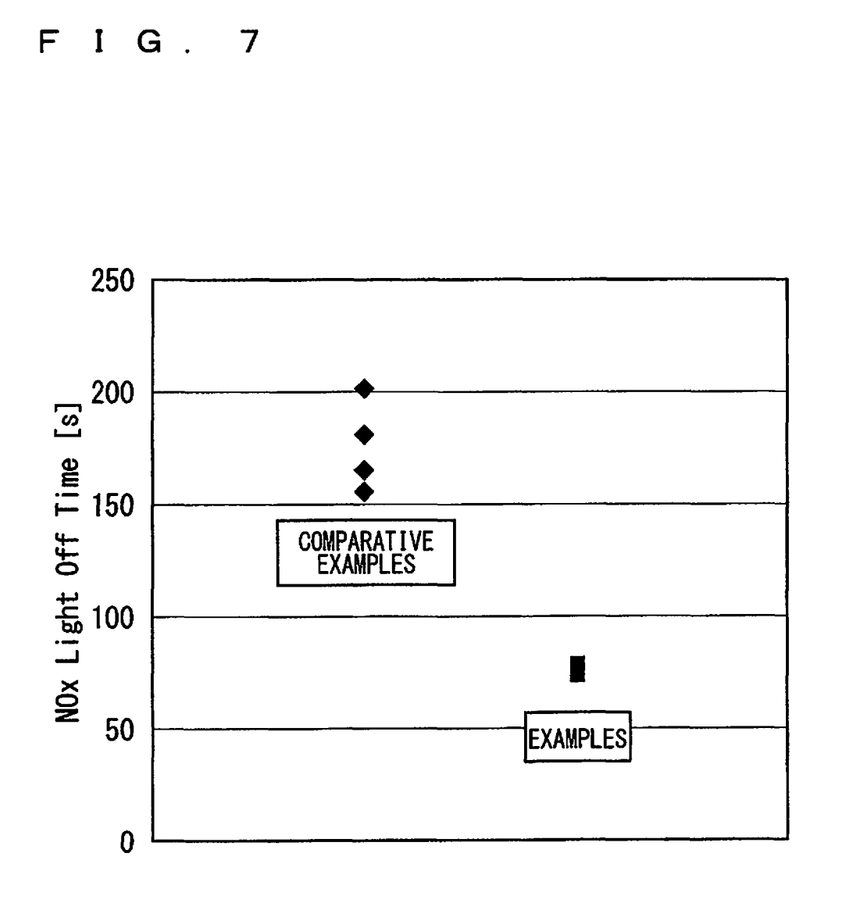
FIG. 7 shows the results of Example 2.

FIG. 7 shows plotted light-off times of the respective sensor elements. In FIG. 7, "EXAMPLES" indicate the results on the sensor elements 101 each including the interlaminar bonding layer 91 provided in the second form, whereas "COMPARATIVE EXAMPLES" indicate the results of the sensor elements each including the interlaminar bonding layer 91 provided in the conventional form.

These results reveal that providing an interlaminar bonding layer 91 in the second form is effective at preventing an increase in light-off time.

What is claimed is:

1. A gas sensor comprising:
a sensor element including a plurality of layers that are bonded and formed of an oxygen-ion conductive solid electrolyte, said gas sensor configured to reduce a predetermined gas component of a measurement gas to identify a concentration of said gas component on the basis of a current flowing through said solid electrolyte;
at least one internal space;
a measuring electrode in one of said at least one internal space and being configured to reduce said gas component of said measurement gas;
a first layer that is one of said plurality of layers and forms a bottom surface of said internal space;
a second layer that is another of said plurality of layers and forms a side surface of said internal space; and
an interlaminar bonding layer bonding said first layer and said second layer,
an exposed surface of said interlaminar bonding layer, that is exposed to said internal space, projecting from said side surface into said internal space such that said exposed surface has a straight-line edge parallel to said side surface in a lamination direction of the plurality of layers.

2. The gas sensor according to claim 1, wherein said at least one internal space includes first to third internal spaces,
said first internal space being in communication with the outside at a predetermined diffusion resistance,
said second internal space being in communication with said first internal space at a predetermined diffusion resistance,
said third internal space having said measuring electrode provided therein and being in communication with said second internal space at a predetermined diffusion resistance.

3. The gas sensor according to claim 1, wherein said interlaminar bonding layer is separate from said measuring electrode.

4. The gas sensor according to claim 1, wherein an edge of said interlaminar bonding layer is in contact with an outer peripheral edge of said measuring electrode.

5. The gas sensor according to claim 1, wherein said interlaminar bonding layer overlaps an outer peripheral portion of said measuring electrode.

6. The gas sensor according to claim 2, wherein said interlaminar bonding layer is separate from said measuring electrode.

7. The gas sensor according to claim 2, wherein an end of said interlaminar bonding layer is in contact with an outer peripheral edge of said measuring electrode.

8. The gas sensor according to claim 2, wherein said interlaminar bonding layer overlaps an outer peripheral portion of said measuring electrode.

9. The gas sensor according to claim 1, further comprising a third layer that is one of said plurality of layers and forms a top surface of said internal space.

10. The gas sensor according to claim 1, wherein the interlaminar bonding layer comprises zirconia.

11. The gas sensor according to claim 1, wherein each of the plurality of layers comprises zirconia.

* * * * *